United States Patent [19]

Parikh et al.

[11] 4,010,250
[45] Mar. 1, 1977

[54] RADIOACTIVE IODINE (125I) LABELING OF LATEX PARTICLES

[75] Inventors: Gokaldas C. Parikh; Chi Kuan Ho, both of Brookings, S. Dak.

[73] Assignee: The United States of America as represented by the Secretary of the Navy, Washington, D.C.

[22] Filed: Mar. 6, 1975

[21] Appl. No.: 556,061

[52] U.S. Cl. .............................. 424/1; 252/301.1 R; 526/21
[51] Int. Cl.² ........................................ A61K 43/00
[58] Field of Search ................. 252/301.1 R; 424/1, 424/12; 260/93.5 A

[56] References Cited

UNITED STATES PATENTS

| | | | |
|---|---|---|---|
| 3,039,977 | 6/1962 | Ingram | 260/93.5 A |
| 3,853,987 | 12/1974 | Dreyer | 424/1 |

OTHER PUBLICATIONS van Oss et al., "The Binding of Immune Globulins . . . Particles," Journal of the Reticuloendothelial Soc., vol. 3, pp. 29–40, (1966).
Keenan et al., General College Chemistry, Harper & Row, Pub., Inc., New York, 1957, p. 559.

*Primary Examiner*—Benjamin R. Padgett
*Assistant Examiner*—Deborah L. Kyle
*Attorney, Agent, or Firm*—Richard S. Sciascia; George A. Montanye

[57] ABSTRACT

The invention disclosed in this application is directed towards developing a radioiodination method which is applicable to the labeling of 2.02 micrometer ($\mu$m) and 0.37 micrometer ($\mu$m) diameter polyvinyltoluene latex particles that have been used as an immunoadsorbent. More particularly the overall method includes using an oxidation-reduction chemical reaction for tagging latex particles. Two methods are described. One, the hydrochloric acid method; and two, the nitric acid method.

2 Claims, 3 Drawing Figures

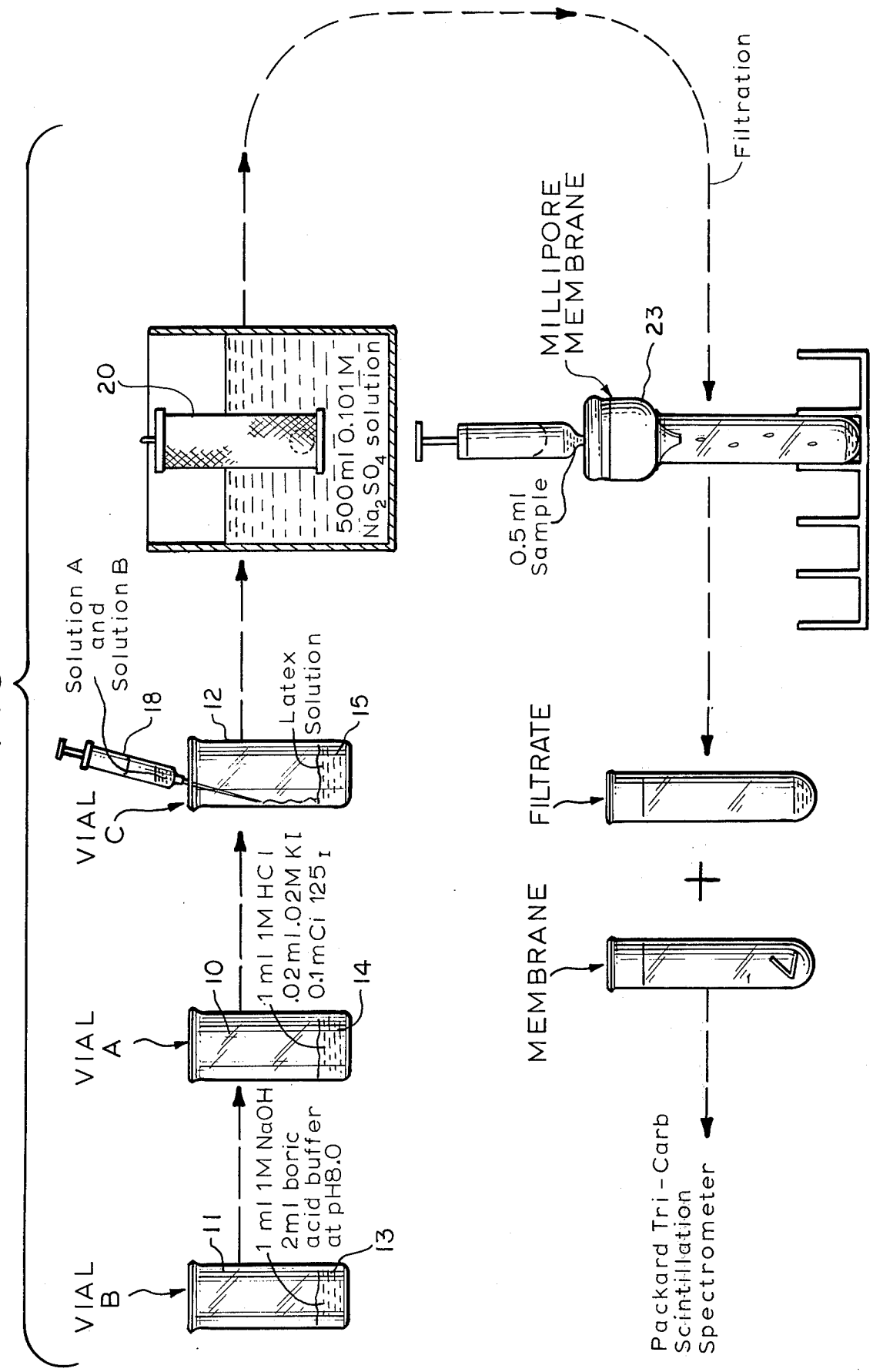

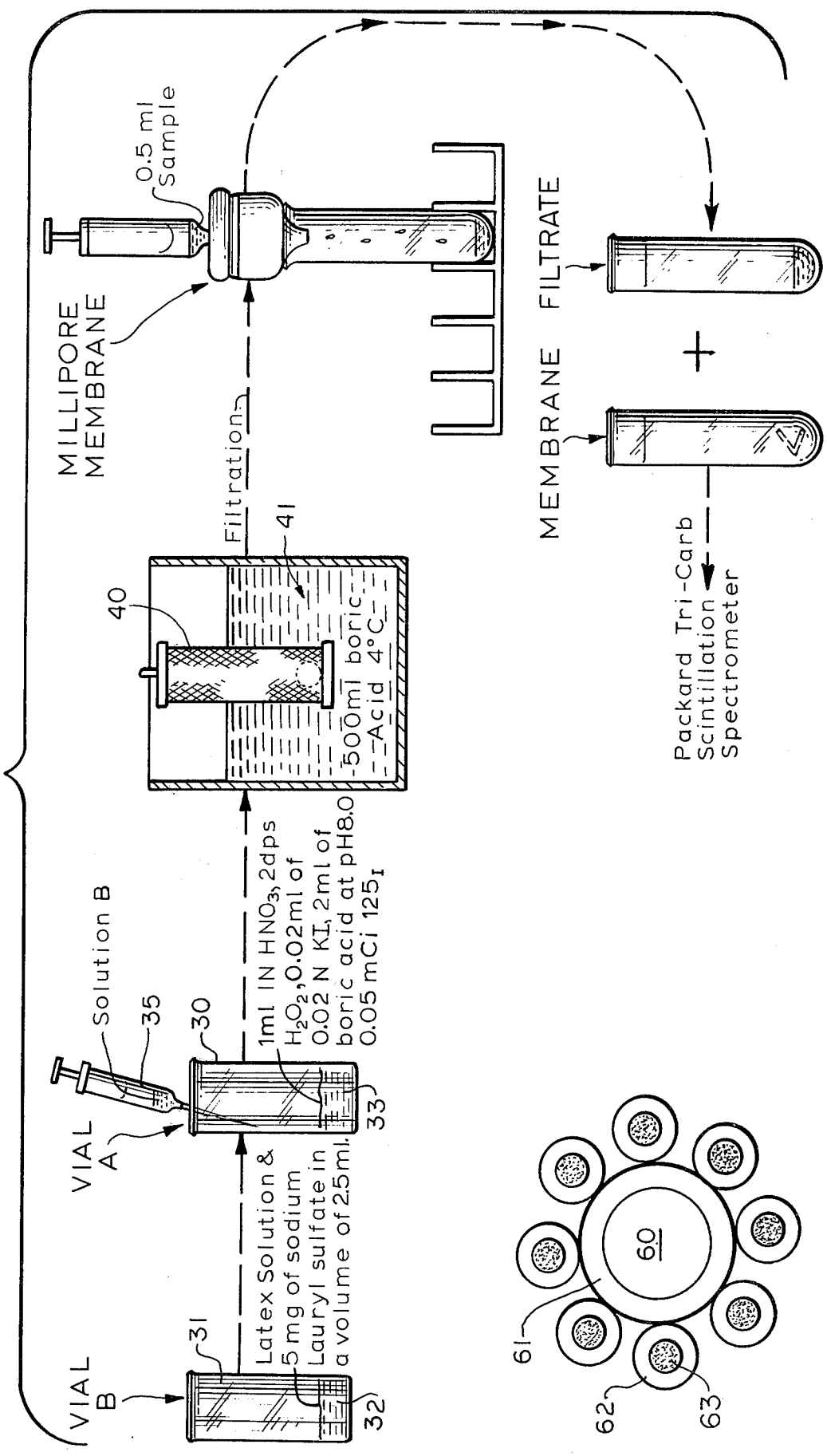

RADIOACTIVE IODINE (125I) LABELING OF LATEX PARTICLES

The invention described herein may be manufactured and used by or for the Government of the United States of America for governmental purposes without the payment of any royalties thereon or therefor.

Many radioiodination methods have been developed in the past few years but none have yet been successfully applied to the labeling of the polyvinyltoluene latex particles.

The method disclosed in this application successfully labels the particles; as a matter of fact, two methods are illustrated in the invention.

It is therefore an object of this invention to provide an improved method for the tagging of latex particles to provide a method of determining quantity of virus present.

It is yet a further object of this invention to provide an improved method of tagging latex particles selecting from the hydrochloric acid method and the nitric acid method.

It is a further object of this invention to provide an improved method of tagging latex particles wherein the method of preparing radioactive iodine ($^{125}I$) labeling of latex particles in a predetermined size range comprises the following steps. Step 1, prepare a first solution which contains 1 ml of 1 N nitric acid ($HNO_3$), 2 drops of concentrated hydrogen peroxide ($H_2O_2$), 0.02 ml of 0.02 N potassium iodide (KI), 2 ml of boric acid buffer at PH 8.0, and 0.05 mCi of carrier-free $^{125}I$. Step 2, prepare a second solution which contains 0.1 ml of 1:200 dilution polyvinyltoluene latex, 5 mg of sodium lauryl sulfate ($CH_3(CH_2)_{10}CH_2SO_4Na$) and 2.4 ml of dionized water. Step 3, add a drop of sodium nitrite to the first chemical solution. Step 4, transfer the first chemical solution to the second chemical solution in drop by drop process, the solution being stirred constantly for a predetermined period of time. Step 5, and 1.02 ml of one normal sodium hydroxide. Step 6, add the material thus compounded to a dialysis bag by a very slow drop by drop process, the material being maintained in the dialysis bag up to 36 hours while suspended in a dialysis solution, the dialysis solution being periodically changed and analyzed. Step 7, the material being removed from the dialysis bag for use subsequently in the process of tagging certain virus.

Still a further object of this invention is to provide an improved method of tagging latex particles wherein the method of preparing radioactive iodine ($^{125}I$) labeling of latex particles in a predetermined size range comprises the following steps. Step 1, prepare a first solution of 1 ml of 1 M sodium hydroxide in 2 ml of boric acid buffer at pH 8.0, step 2, prepare a second solution containing 1 ml of 1 M HCl, 0.02 ml of 0.02 N potassium iodide and 0.1 mCi of carrier-free $^{125}I$, step 3 prepare a third solution which contains 0.1 ml of 1:200 (2.02$\mu$m) latex suspended in 2.4 ml of boric acid buffer at pH 8.0, step 4, add a drop of 0.1N sodium nitrite to the first solution and stir, step 5, combine the first and second solutions, step 6, combine the first and second solutions into the third solution in a drop by drop process and stir for at least 10 minutes, step 7, pipette the material thus compounded into a dialysis bag step 8, maintain the material in the dialysis bag up to 36 hours while it is suspended in a dialysis solution, the dialysis solution being periodically changed and analyzed.

Other objects, advantages and novel features of the invention will become apparent from the following detailed description of the invention when considered in conjunction with the accompanying drawings wherein:

FIG. 1, is the flow diagram of the method of radioiodination of latex utilizing the hydrochloric acid method.

FIG. 2, is the radioiodination method utilizing the nitric acid method.

FIG. 3, is the schematic presentation of the coated latex antibody method.

FIG. 1, illustrates the hydrochloric acid method of preparation of the latex particles. The first step of the method includes preparation of solutions in containers, 10, 11, and 12. The solution in container 10 contains 1 ml of 1 M HCl, 0.02 ml of 0.02 M potassium iodide and 0.1 mCi of carrier-free $^{125}I$.

The second container 11, is a solution which contains 1 ml of 1 M sodium hydroxide in 2 ml of boric acid buffer at pH 8.0.

Container 12 has the third solution and contains 0.1 ml of 1:200 (2.02 $\mu$m) latex suspended in 2.4 ml of boric acid buffer at pH 8.0. Each of the 3 containers has a magnetic stirrer 13, 14 and 15 respectively to provide for the stirring of the individual solutions.

After these three solutions have been prepared, the next step is to add one drop of 0.1 N sodium nitrite to the solution in container 10. This will be stirred thoroughly by the magnetic stirrer 14 and the solution will acquire a brown color at this step of the process.

Next, the solution in container 11 is poured into the material in container 10. The combination of the two solutions should have a pH at this point which should be approximately 8.0.

A syringe 18 is utilized to transfer the commingled solutions from 10 and 11 drop by drop into the solution in container 12 which of course is stirred continuously.

The stirring continues for approximately 10 minutes and the solution in container 12 is pipetted into a dialysis bag 20. (Spectrapor membrane tubing with cylinder diameter of 25.5 mm and a molecular weight cutoff of 6,000 to 8,000. Spectrum Med. Ind. Inc. Los Angles) for dialysis against 500 ml of 0.1 M sodium sulfate solution in the cold room (4° C).

The dialysis solution (sodium sulfate) is constantly stirred by a magnetic stirrer and it is advisable to change the dialysis solution every twelve hours. The dialysis solution should be tested for free $^{125}I$ every time a change is made in the solution. At the end of a 36 hour period the contents of the dialysis bag 20 are placed in a plastic tube and kept at a lower temperature of −20° C for future use. A half-ml sample of this solution should be taken for radioactive counting.

A 0.5 ml sample is filtered thru a Millipore membrane (0.45 $\mu$m) 23 and washed twice with two 0.5 ml portions of distilled water. Then count the filtrate and millipore membrane respectively. The number of counts on the membrane indicates the amount of $^{125}I$ atoms tagged on to the latex particles.

The second method of tagging is a nitric acid-hydrogen peroxide method. This method includes preparing a first solution in a container 30 which contains 1 ml of 1 N nitric acid ($HNO_3$), 2 drops of concentrated hydrogen peroxide ($H_2O_2$), 0.02 ml of 0.02 N potassium iodide (KI), 2 ml of boric acid buffer at pH 8.0, and 0.05 mCi of carrier-free $^{125}I$.

In a second container 31 a second solution is prepared which contains 0.1 ml of 1:200 dilution polyvinyltoluene latex, 5 mg of sodium lauryl sulfate (CH$_3$(CH$_2$)$_{10}$CH$_2$SO$_4$Na) and 2.4 ml of dionized water. The solutions are stirred constantly by magnetic stirrers 32 and 33.

The next step in this method is to add a drop of sodium nitrite (NaNO$_2$) to container 30. Then the solution in container 31 is transferred to the solution in container 30 drop by drop by means of syringe 35. The solution is continuously stirred for approximately 10 minutes and then 1.02 ml of 1N sodium hydroxide(NaOH) is added.

The material in container 30 is emptied into a dialysis bag and allowed to dialyze against 500 ml of boric acid buffer at pH 8.0 in a beaker at 4° C.

The dialysis solution 41 is changed every 12 hours and 0.5 ml of dialysis solution is collected before each change. After 36 hours the solution in the dialysis bag 40 is transferred to a plastic tube for storage and a 0.5 ml sample for radioactivity counting by the scintillation counter. (not shown).

The next step is to filter the sample thru a 0.45$\mu$m Millipore filter 50 and then count the filtrate and the membrane.

The result of the latex labeling of the two methods are set forth in Table 1.

Table 1

Result of Polyvinyltoluene (2.02$\mu$m) latex labeling by $^{125}$I

| | Hydrochloric Acid Method | Nitric Acid Method |
|---|---|---|
| Background | 447 | 447 |
| | 438 | 438 |
| | 486 | 486 |
| Dialysis I | 31,889 | 39,812 |
| | 31,883 | 40,061 |
| | 31,804 | 39,998 |
| Dialysis II | 1,216 | 3,369 |
| | 1,182 | 3,286 |
| | 1,120 | 3,279 |
| Dialysis III | 810 | 1,273 |
| | 781 | 1,323 |
| | 805 | 1,326 |
| In dialysis sac | 77,722 | 101,190 |
| | 78,346 | 100,749 |
| | 79,246 | 100,959 |
| Filtrate | 4,508 | 45,536 |
| | 4,555 | 45,043 |
| | 4,612 | 45,533 |
| Membrane | 54,256* | 40,485* |
| | 53,801* | 40,572* |
| | 53,786* | 40,543* |
| Mean | 53,948 | 40,533 |
| Standard deviation | 267.13 | 44.3 |
| % Standard deviation | 0.50 | 0.109 |

*Standard deviation of the above data was calculated to assure the reliability of the scintillation counter with 99% confidence limit.

FIG. 3, is an illustration of the coated latex adsorption method (CLAM) for the detection of viruses, antibodies, enzymes and toxins.

As can be seen, the basic procedure is to have an inert latex particle 60, upon which a specific antibody coating 61 has been placed. The adsorbed viruses 62 coated on nucleic acid core 63 attach themselves to the antibody coating and by their increased volume (volume displacement) or by increaed radioisotope tagging (radioimmunoassay) it can determine what is in the various samples to be tested.

The possibility of tagging inert latex particles with $^{125}$I, can amplify the radioactive signal and thus increase the sensitivity of this detection method.

Obviously, many modifications and variations of the present invention are possible in the light of the above teachings. It is therefore to be understood that within the scope of the appended claims, the invention may be practiced otherwise than as specifically described.

We claim:

1. The method of preparing radioactive iodine 125 labeled latex particles of polyvinyl toluene in a predetermined size range of 2.02 $\mu$m to 0.37 $\mu$m in diameter comprising the following steps:

Step 1, prepare a first solution which contains 1 ml of 1 N nitric acid, 2 drops of concentrated hydrogen peroxide, 0.02 ml of 0.02 N potassium iodide, 2 ml of boric acid buffer at pH 8.0, and 0.05 mCi of carrier-free $^{125}$I;

Step 2, prepare a second solution which contains 0.1 ml of 1:200 dilution polyvinyltoluene latex, 5 mg of sodium lauryl sulfate and 2.4 ml of dionized water;

Step 3, add a drop of 0.1 N sodium nitrite to said first chemical solution;

Step 4, transfer said first chemical solution to said second chemical solution in a drop by drop process, said solution being stirred constantly for a predetermined period of time;

Step 5, add 1.02 ml of 1 N sodium hydroxide;

Step 6, add the material thus compounded to a dialysis bag by a very slow drop by drop process, said material being maintained in said dialysis bag up to 36 hours while suspended in a dialysis solution of boric acid, said dialysis solution being periodically changed and analyzed;

Step 7, said material being removed from said dialysis bag for use subsequently in the process of tagging certain virus.

2. The method of preparing radioactive iodine 125 labeled latex particles of polyvinyltoluene in a predetermined size range of 2.02 $\mu$m to 0.37 $\mu$m in diameter comprisng the following steps:

Step 1, preparing a first solution of 1 ml of 1 M sodium hydroxide in 2 ml of boric acid buffer at pH 8.0;

Step 2, preparing a second solution containing 1 ml of 1 M HCl, 0.02 ml of 0.02 N potassium iodide and 0.1 mCi of carrier-free $^{125}$I;

Step 3, preparing a third solution which contains 0.1 ml of 1:200 dilution latex suspended in 2.4 ml of boric acid buffer at pH 8.0;

Step 4, add a drop of 0.1 N sodium nitrite to said first solution and stir;

Step 5, combine the first and second solutions;

Step 6, add the thus produced solution to the third solution in a drop by drop process and stir for at least 10 minutes;

Step 7, pipette the material thus compounded into a dialysis bag;

Step 8, maintain said material in said dialysis bag up to 36 hours while it is suspended in a dialysis solution of sodium sulfate, said dialysis solution being periodically changed and analyzed.

* * * * *

UNITED STATES PATENT OFFICE
CERTIFICATE OF CORRECTION

Patent No. 4,010,250            Dated     March 1, 1977

Inventor(s) Gokaldas C. Parikh et al.

It is certified that error appears in the above-identified patent and that said Letters Patent are hereby corrected as shown below:

In the Abstract: cancel line 1; line 2 cancel "towards developing a" and substitute -- A -- therefore and cancel "which is"; line 8 cancel ". One" and substitute -- ; namely -- therefore; line 9 cancel "two, ".

Column 1 insert -- Background of the Invention -- between lines 7 and 8; line 14 cancel "in the invention"; line 20 insert -- by -- after "particles"; line 31 change "PH8.0" to -- pH 8.0 --; line 35 change "dionized" to -- deionized -- and insert -- ($NaNO_2$) -- after "nitrite"; line 59 change "(2.02 μm)" to -- (2.02 μm or 0.37 μm) --; line 60 change "0.1N" to -- 0.1 N --.

Column 2 line 23 change "(2.02 μm)" to -- (2.02 μm or 0.37 μm) --; line 34 insert -- final -- after "a" and cancel "at this point which should"; line 35 change "be" to -- of --; line 53 cancel "lower"; line 62 insert -- Referring to Fig. 2, the -- in place of "The".

Column 3 line 4 change "dionized" to -- deionized --; line 25 change "filter" to -- membrane --; in Table 1 change "In dialysis sac" to -- In dialysis bag --; line 63 change "coated on" to -- with their -- and change "core" to -- cores --.

Column 4 line 13 change "polyvinyl toluene" to -- polyvinyltoluene --;

Signed and Sealed this

Sixth Day of December 1977

[SEAL]

Attest:

RUTH C. MASON        LUTRELLE F. PARKER
*Attesting Officer*      *Acting Commissioner of Patents and Trademarks*